(12) United States Patent
Uesugi

(10) Patent No.: US 12,426,942 B2
(45) Date of Patent: Sep. 30, 2025

(54) TREATMENT TOOL AND TREATMENT TOOL ASSEMBLY METHOD

(71) Applicant: Olympus Corporation, Tokyo (JP)

(72) Inventor: Kenji Uesugi, Sagamihara (JP)

(73) Assignee: Olympus Corporation, Tokyo (JP)

( * ) Notice: Subject to any disclaimer, the term of this patent is extended or adjusted under 35 U.S.C. 154(b) by 294 days.

(21) Appl. No.: 18/056,130

(22) Filed: Nov. 16, 2022

(65) Prior Publication Data
US 2023/0071864 A1    Mar. 9, 2023

Related U.S. Application Data

(63) Continuation of application No. PCT/JP2020/020011, filed on May 20, 2020.

(51) Int. Cl.
*A61B 18/14* (2006.01)
*A61B 17/00* (2006.01)
(Continued)

(52) U.S. Cl.
CPC .. *A61B 18/1445* (2013.01); *A61B 17/320092* (2013.01); *A61B 18/1447* (2013.01);
(Continued)

(58) Field of Classification Search
CPC ........... A61B 17/320092; A61B 2017/320094; A61B 2017/2919; A61B 2017/2902;
(Continued)

(56) References Cited

U.S. PATENT DOCUMENTS 5,683,413 A * 11/1997 Miyagi ............. A61B 1/00137
606/208
2011/0288579 A1   11/2011 Hyodo
(Continued)

FOREIGN PATENT DOCUMENTS

JP    2004129871 A    4/2004
JP    2011189185 A    9/2011
(Continued)

OTHER PUBLICATIONS

"International Application Serial No. PCT/JP2020/020011, International Search Report dated Jul. 14, 2020", (Jul. 14, 2020), 2 pgs.

*Primary Examiner* — Darwin P Erezo
*Assistant Examiner* — Raihan R Khandker
(74) *Attorney, Agent, or Firm* — Schwegman Lundberg & Woessner, P.A.

(57) ABSTRACT

A treatment tool includes: a pair of grippers configured to grip living tissue, at least one of the pair of grippers being configured in an openable and closable manner; a transmission portion connected to the at least one of the pair of grippers, the transmission portion being configured to move forward and backward along a first direction to open and close the pair of grippers; an operating portion configured to receive user operation for gripping the living tissue; an elastic body configured to transmit, to the transmission portion, an operating force applied to the operating portion by the user operation while being compressively deformed in accordance with the operating force; and an adjustment mechanism configured to adjust an amount of compressive deformation of the elastic body when the user operation is performed on the operating portion, to thereby adjust a gripping force of the pair of grippers.

21 Claims, 13 Drawing Sheets

(51) Int. Cl.
  *A61B 17/29*  (2006.01)
  *A61B 17/32*  (2006.01)
  *A61B 18/00*  (2006.01)

(52) U.S. Cl.
  CPC ............... *A61B 2017/00862* (2013.01); *A61B 2017/2932* (2013.01); *A61B 2017/320082* (2017.08); *A61B 2017/320094* (2017.08); *A61B 2017/320095* (2017.08); *A61B 2018/00589* (2013.01); *A61B 2018/00601* (2013.01)

(58) Field of Classification Search
  CPC .... A61B 2017/2932; A61B 2017/2922; A61B 2017/2924; A61B 2017/2912
  See application file for complete search history.

(56) References Cited

U.S. PATENT DOCUMENTS

2018/0360458 A1* 12/2018 Tapia Espriu ......... A61B 17/08
2020/0353632 A1* 11/2020 Steinthorsson ...... B25J 15/0028

FOREIGN PATENT DOCUMENTS

| JP | 2011239922 A | 12/2011 |
| JP | 2012200415 A | 10/2012 |

\* cited by examiner

TREATMENT TOOL AND TREATMENT TOOL ASSEMBLY METHOD

CROSS-REFERENCE TO RELATED APPLICATION

This application is a continuation of International Application No. PCT/JP2020/020011, filed on May 20, 2020, the entire contents of which are incorporated herein by reference.

BACKGROUND

1. Technical Field

The present disclosure relates to a treatment tool and a treatment tool assembly method.

2. Related Art

In the related art, a treatment tool that applies energy to a region to be treated (hereinafter, described as a target region) in living tissue and performs treatment on the target region is known (for example, see Japanese Laid-open Patent Publication No. 2011-189185).

In the treatment tool described in Japanese Laid-open Patent Publication No. 2011-189185, a clamp member is configured in an openable and closable manner with respect to a distal end portion of a blade. Further, the target region is gripped by closing the clamp member with respect to the distal end portion of the blade. In the following, the distal end portion of the blade and the clamp member will be referred to as a pair of grippers.

SUMMARY

In some embodiments, a treatment tool includes: a pair of grippers configured to grip living tissue, at least one of the pair of grippers being configured in an openable and closable manner; a transmission portion that is connected to the at least one of the pair of grippers, the transmission portion being configured to move forward and backward along a first direction to open and close the pair of grippers; an operating portion configured to receive user operation for gripping the living tissue; an elastic body configured to transmit, to the transmission portion, an operating force applied to the operating portion by the user operation while being compressively deformed in accordance with the operating force; and an adjustment mechanism configured to adjust an amount of compressive deformation of the elastic body when the user operation is performed on the operating portion, to thereby adjust a gripping force of the pair of grippers, the adjustment mechanism including a contact portion configured to be in contact with the elastic body; and a pair of tables configured to be in contact with the contact portion, the pair of tables being configured to approach or separate from each other to adjust a position of the contact portion and adjust the amount of compressive deformation of the elastic body when the user operation is performed on the operating portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for carrying out the disclosure (hereinafter, embodiments) will be described below with reference to the drawings. The disclosure is not limited by the embodiments described below. In addition, in description of the drawings, the same components are denoted by the same reference symbols.

First Embodiment

Overall Configuration of Treatment System

Figure 1:
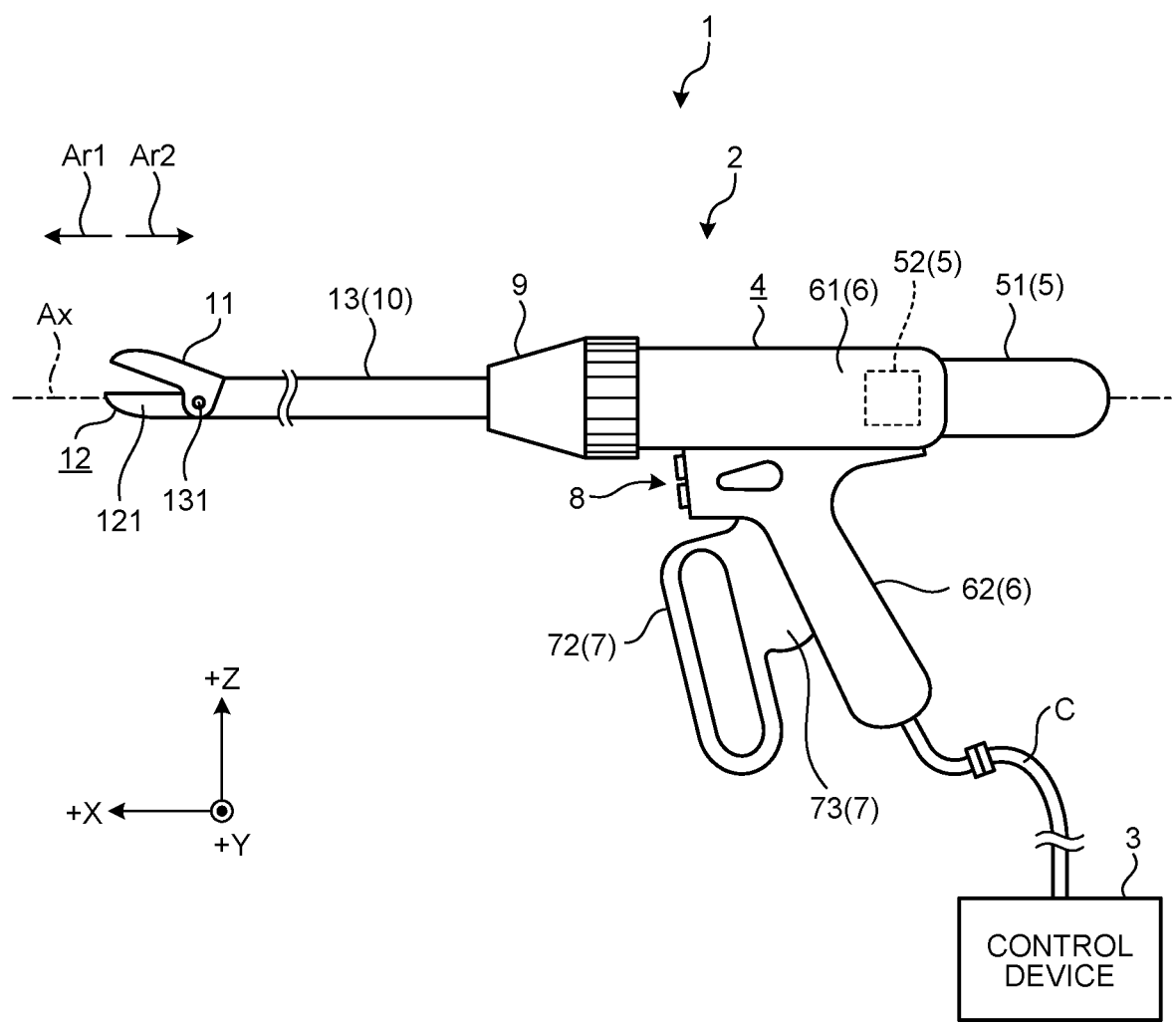
FIG. 1 is a diagram illustrating a treatment system according to a first embodiment.

FIG. 1 is a diagram illustrating an overall configuration of a treatment system 1 according to a first embodiment.

The treatment system 1 applies ultrasonic energy and high-frequency energy to a region to be treated (hereinafter, described as a target region) in living tissue and performs treatment on the target region. Meanwhile, the treatment that is available by the treatment system 1 according to the first embodiment is treatment for coagulating (sealing) the target region, treatment for incising the target region, treatment for performing coagulation and incision at the same time, or the like. Further, as illustrated in FIG. 1, the treatment system 1 includes a treatment tool 2 and a control device 3.

Configuration of Treatment Tool

In the following description of a configuration of the treatment tool 2, XYZ coordinate axes, that is, an X-axis, a Y-axis, and a Z-axis that are perpendicular to one another are used. The X-axis is an axis parallel to a central axis Ax (FIG. 1) of a sheath 10. A direction along the central axis Ax corresponds to a first direction. The Y-axis is an axis perpendicular to the sheet of FIG. 1. The Z-axis is an axis along the vertical direction in FIG. 1. Further, in the following, one side along the central axis Ax (positive X-axis side) will be described as a distal end side Ar1, and the other side (negative X-axis side) will be described as a proximal end side Ar2.

Figure 2:
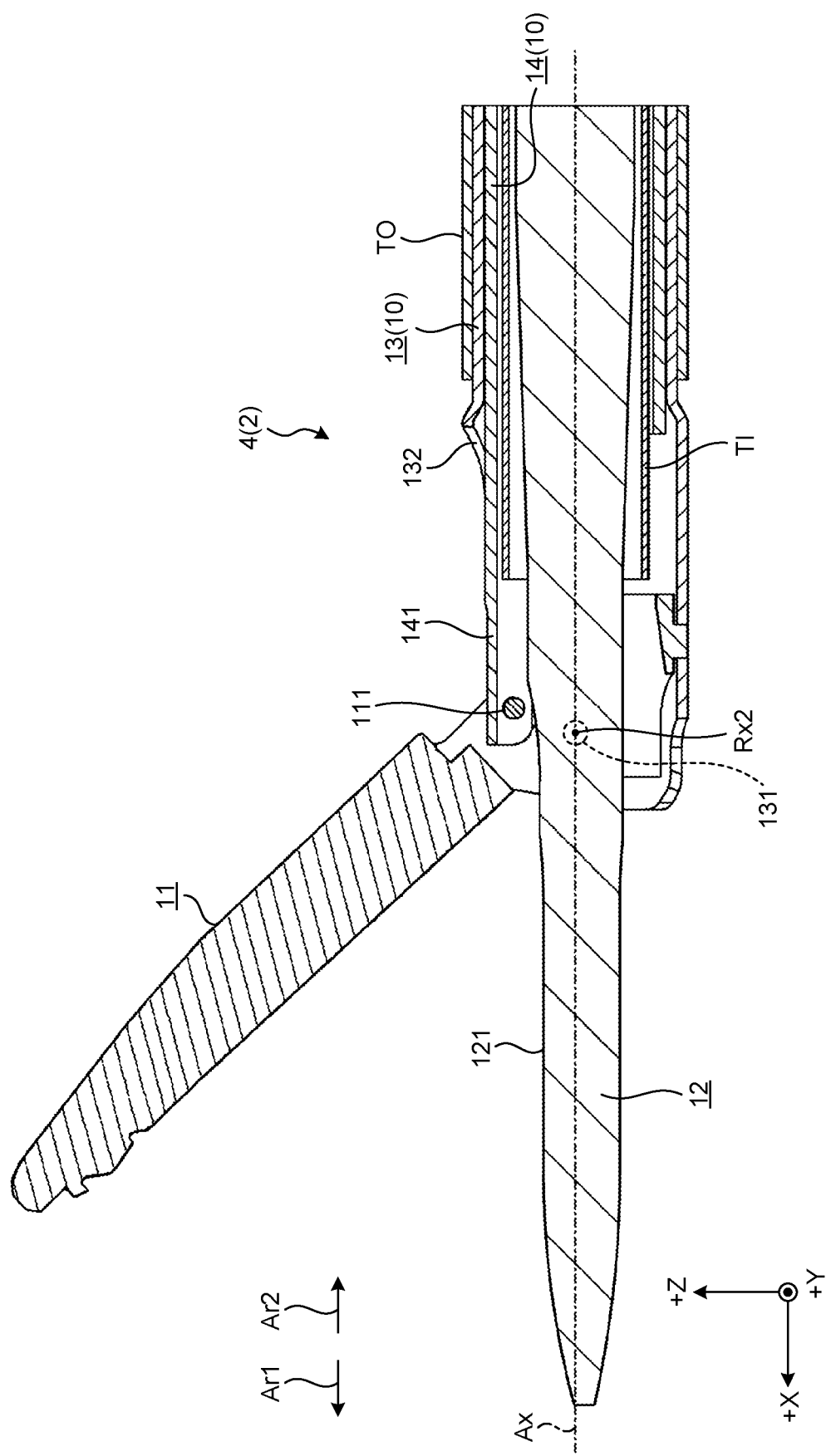
FIG. 2 is a diagram for explaining a configuration of a treatment tool.
Figure 3:
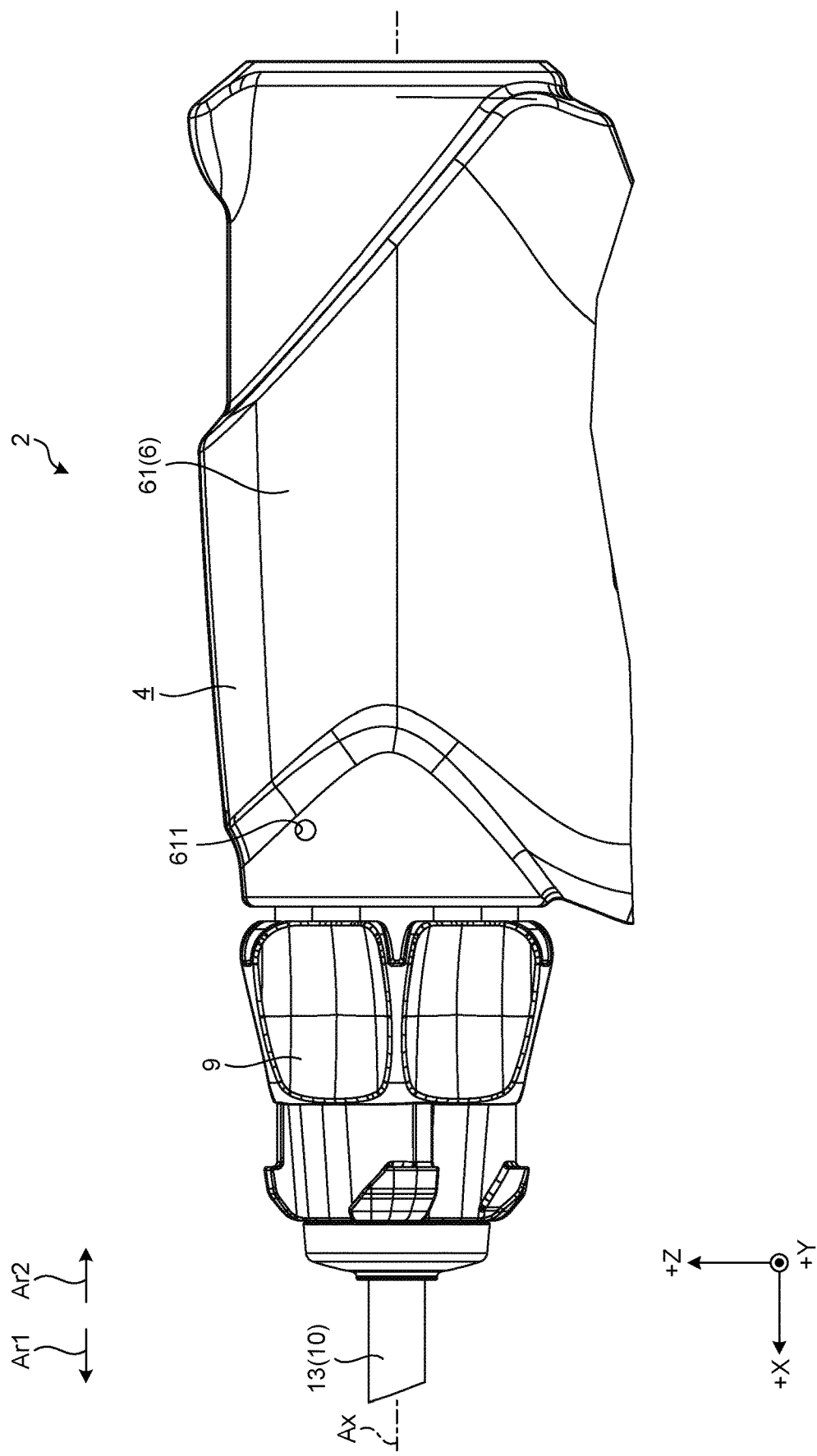
FIG. 3 is a diagram for explaining the configuration of the treatment tool.
Figure 4:
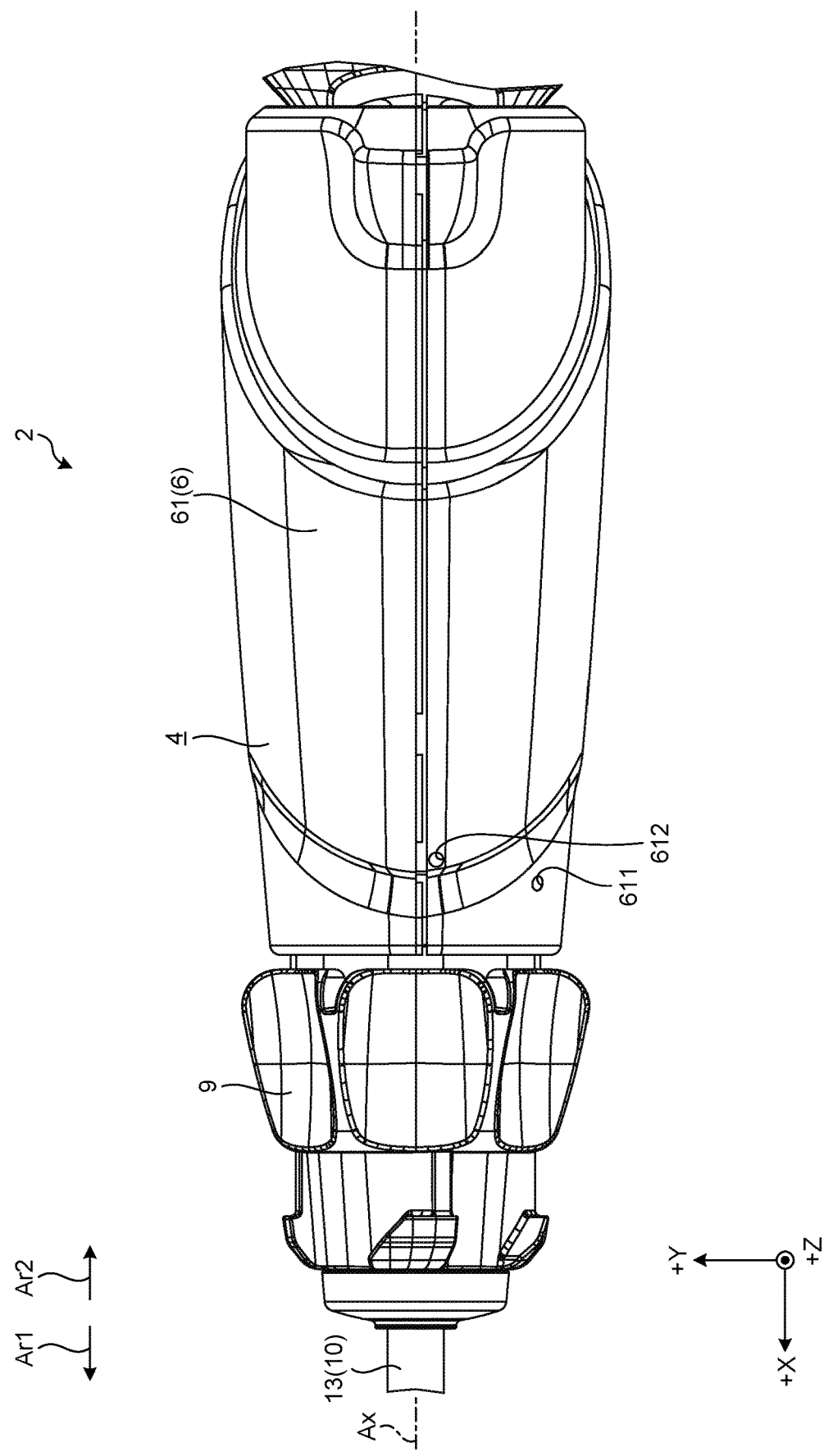
FIG. 4 is a diagram for explaining the configuration of the treatment tool.
Figure 5:
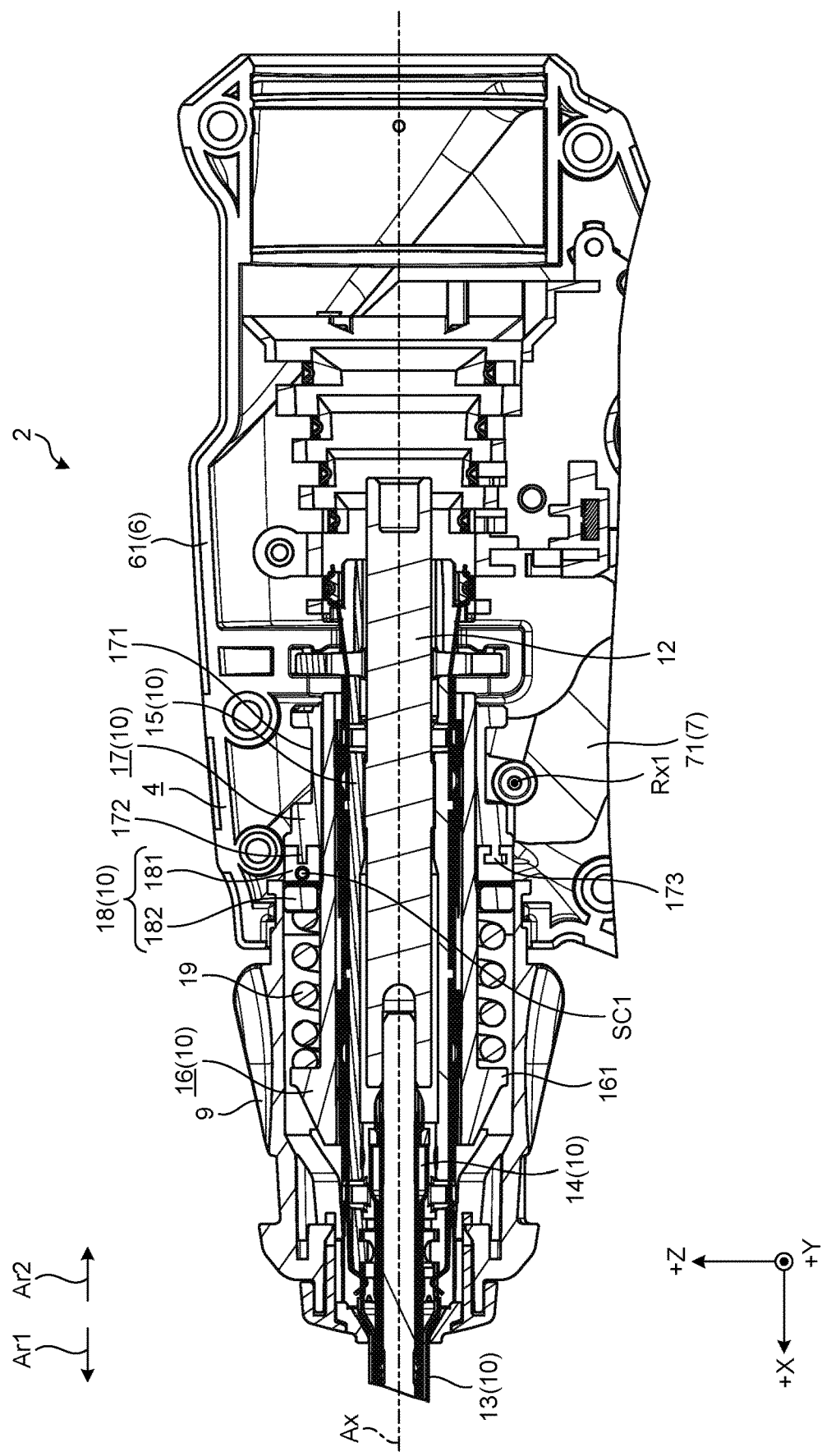
FIG. 5 is a diagram for explaining the configuration of the treatment tool.

FIG. 2 to FIG. 5 are diagrams for explaining the configuration of the treatment tool 2. Specifically, FIG. 2 is a cross-sectional view of a portion of the treatment tool 2 at the distal end side Ar1. FIG. 3 is a diagram illustrating a portion of the treatment tool 2 at the proximal end side Ar2 when viewed from a positive Y-axis side (from the front side of the sheet of FIG. 1). FIG. 4 is a diagram illustrating the portion of the treatment tool 2 at the proximal end side Ar2 when viewed from a positive Z-axis side (from the upper side in FIG. 1). FIG. 5 is a cross-sectional view of an internal structure of the portion of the treatment tool 2 at the proximal end side Ar2. Meanwhile, in FIG. 3 to FIG. 5, illustration of an ultrasonic transducer 5 is omitted for convenience of explanation.

The treatment tool 2 is an ultrasonic treatment tool that applies ultrasonic energy and high-frequency energy to a target region and performs treatment on the target region. As illustrated in FIG. 1 to FIG. 5, the treatment tool 2 includes a hand piece 4 and the ultrasonic transducer 5 (FIG. 1).

As illustrated in FIG. 1 to FIG. 5, the hand piece 4 includes a holding case 6 (FIG. 1 and FIG. 3 to FIG. 5), a movable handle 7 (FIG. 1 and FIG. 5), a switch 8 (FIG. 1), a rotation knob 9 (FIG. 1 and FIG. 3 to FIG. 5), the sheath 10, a jaw 11 (FIG. 1 and FIG. 2), and a vibration transmission portion 12 (FIG. 1, FIG. 2, and FIG. 5).

The holding case 6 is a member that forms an external appearance of the treatment tool 2 and covers an adjustment mechanism 18 (to be described later), and corresponds to a cover. The holding case 6 supports the entire treatment tool 2. Further, as illustrated in FIG. 1 and FIG. 3 to FIG. 5, the holding case 6 includes a holding case main body 61 that is coaxial with the central axis Ax and that has an approximately cylindrical shape, and a fixed handle 62 that extends from the holding case main body 61 to a negative Z-axis side and that is held by an operating person, such as an operator.

A first through hole 611 (FIG. 3) and a second through hole 612 (FIG. 4) are arranged in the holding case main body 61.

The first through hole 611 corresponds to a through hole. As illustrated in FIG. 3, the first through hole 611 is located at the distal end side Ar1 on the holding case main body 61 and penetrates through inside and outside of the holding case main body 61 along the Y axis from the positive Y-axis side. Further, the operator is able to access a first screw SC1 (to be described later), which is arranged inside the holding case main body 61, through the first through hole 611.

As illustrated in FIG. 4, the second through hole 612 is located at the distal end side Ar1 on the holding case main body 61 and penetrates through the inside and the outside of the holding case main body 61 along the Z axis from the positive Z-axis side. Further, the operator is able to access a second screw SC2 (to be described later), which is arranged inside the holding case main body 61, through the second through hole 612.

The movable handle 7 corresponds to an operating portion The movable handle 7 receives closing operation (corresponding to user operation) and opening operation that are performed by the operating person, such as the operator. Further, as illustrated in FIG. 1 or FIG. 5, the movable handle 7 includes a handle base portion 71 (FIG. 5), an operating unit 72 (FIG. 1), and a connection portion 73 (FIG. 1).

The handle base portion 71 is located inside the holding case 6. Further, a portion of the handle base portion 71 at the positive Z-axis side is pivotally supported by the holding case 6 so as to be rotatable about a first rotation axis Rx1 (FIG. 5) that is parallel to the Y axis. Furthermore, a pair of protruding portions 711 (see FIG. 6) that are bifurcated portions, that protrude toward the positive Z-axis, and that engage with a slider 17 (to be described later) are arranged on an end portion of the handle base portion 71 at the positive Z-axis side.

The operating unit 72 is a portion that receives the closing operation and the opening operation performed by the operating person, such as the operator, and is located outside the holding case 6 as illustrated in FIG. 1.

The connection portion 73 is a portion that is arranged across the inside and outside of the holding case 6, and connects the handle base portion 71 and the operating unit 72.

If the movable handle 7 receives the closing operation that is performed by the operating person, such as the operator, the movable handle 7 rotates in a counterclockwise direction about the first rotation axis Rx1 in FIG. 5. Namely, the operating unit 72 moves in a direction approaching the fixed handle 62. In contrast, if the movable handle 7 receives the opening operation, the movable handle 7 rotates in a clockwise direction about the first rotation axis Rx1 in FIG. 5. Namely, the operating unit 72 moves in a direction moving away from the fixed handle 62.

As illustrated in FIG. 1, the switch 8 is arranged so as to be exposed to the outside from a side face of the fixed handle 62 at the distal end side Ar1. Further, the switch 8 receives treatment operation that is performed by the operating person, such as the operator. The treatment operation is operation of applying ultrasonic energy or high-frequency energy to a target region.

The rotation knob 9 has an approximately cylindrical shape that is coaxial with the central axis Ax, and is arranged at the distal end side Ar1 on the holding case main body 61 as illustrated in FIG. 1 and FIG. 3 to FIG. 5. Further, the rotation knob 9 receives rotation operation that is performed by the operating person, such as the operator. Through the rotation operation, the rotation knob 9 rotates about the central axis Ax with respect to the holding case main body 61. Further, with the rotation of the rotation knob 9, the jaw 11 and the vibration transmission portion 12 rotate about the central axis Ax.

The entire sheath 10 has an approximately cylindrical shape. As illustrated in FIG. 1 to FIG. 5, the sheath 10 includes an outer pipe 13, an inner pipe 14 (FIG. 2 and FIG. 5), a holder portion 15 (FIG. 5), a slider receiver 16 (FIG. 5), the slider 17 (FIG. 5), and the adjustment mechanism 18 (FIG. 5).

The outer pipe 13 is a cylindrical pipe that is made of a metal material or the like.

An outer peripheral surface of the outer pipe 13 is covered by an outer tube TO (FIG. 2) with electrical insulation property.

Further, a first pin 131 (FIG. 1 and FIG. 2) that extends along the Y axis and that pivotally supports the jaw 11 such that the jaw 11 is rotatable about a second rotation axis Rx2 (FIG. 2) is fixed to an end portion of the outer pipe 13 at the distal end side Ar1.

Furthermore, a notch portion 132 (FIG. 2) that extends from a distal end to the proximal end side Ar2 is formed on the end portion of the outer pipe 13 at the distal end side Ar1 and at the positive Z-axis side.

The inner pipe 14 is a cylindrical pipe with a smaller diameter than the outer pipe 13. Further, the inner pipe 14 is inserted in the outer pipe 13 so as to be coaxial with the outer pipe 13.

As illustrated in FIG. 2, an arm portion 141 that protrudes toward the distal end side Ar1 is arranged on an end portion of the inner pipe 14 at the distal end side Ar1 and at the positive Z-axis side. A second pin 111 that is arranged on the jaw 11 and that extends so as to be parallel to the second rotation axis Rx2 (the first pin 131) is inserted in the arm portion 141.

The holder portion 15 is configured with a certain material, such as resin, with electrical insulation property and has an approximately cylindrical shape. As illustrated in FIG. 5, the holder portion 15 is inserted in the rotation knob 9 and the holding case main body 61 across the rotation knob 9 and the holding case main body 61. Further, the holder portion 15 holds the vibration transmission portion 12 that is inserted in the holder portion 15. Furthermore, an end portion of the holder portion 15 at the distal end side Ar1 is mechanically connected to the rotation knob 9 and the outer pipe 13. Namely, the holder portion 15, the outer pipe 13, the jaw 11, and the vibration transmission portion 12 rotate about the central axis Ax together with the rotation knob 9, in accordance with the rotation operation that is performed on the rotation knob 9 by the operating person, such as the operator.

The slider receiver 16 is configured with a certain material, such as resin, with electrical insulation property and has an approximately cylindrical shape. Further, the slider receiver 16 is arranged so as to be movable along the central axis Ax relative to the holder portion 15 while the holder portion 15 is inserted in the slider receiver 16. Here, an end portion of the slider receiver 16 at the distal end side Ar1 is connected to an end portion of the inner pipe 14 at the proximal end side Ar2 such that the slider receiver 16 is allowed to move along the central axis Ax relative to the holder portion 15 and restricted from rotating about the central axis Ax. Namely, the slider receiver 16 and the inner pipe 14 rotate about the central axis Ax together with the rotation knob 9, in accordance with the rotation operation that is performed on the rotation knob 9 by the operating person, such as the operator.

An opposing portion 161 (FIG. 5) that extends outward along a radial direction and that has an annular shape is arranged on an outer peripheral surface of the slider receiver 16.

The slider 17 has an approximately cylindrical shape and is arranged so as to be movable along the central axis Ax relative to the slider receiver 16 while the slider receiver 16 is inserted in the slider 17.

A groove 171 that is recessed toward the central axis Ax and that has an annular shape extending along a rotation direction about the central axis Ax is arranged on an outer peripheral surface of the slider 17. Further, the slider 17 engages with the pair of protruding portions 711 when the pair of protruding portions 711 of the movable handle 7 is inserted in the groove 171.

Further, the slider 17, the slider receiver 16, and the inner pipe 14 operate as described below in accordance with operation that is performed on the movable handle 7 by the operating person, such as the operator.

The slider 17 is pushed by the pair of protruding portions 711 of the movable handle 7 toward the distal end side Ar1 along the central axis Ax, in accordance with the closing operation that is performed on the movable handle 7 by the operating person, such as the operator. Further, the slider 17 compressively deforms a coil spring 19 (FIG. 5) that is arranged between the opposing portion 161 and the slider receiver 16. Furthermore, the slider receiver 16 receives a pressing force from the slider 17 toward the distal end side Ar1 via the coil spring 19. Moreover, the inner pipe 14 moves toward the distal end side Ar1 along the central axis Ax in conjunction with the slider receiver 16. Furthermore, the arm portion 141 pushes the second pin 111 toward the distal end side Ar1. Then, the jaw 11 rotates in the counter-clockwise direction about the second rotation axis Rx2 in FIG. 2. At this time, the second pin 111 moves while maintaining a constant distance from the second rotation axis Rx2, so that the arm portion 141 moves to the distal end side Ar1 while being deformed toward the positive Z-axis side at which the notch portion 132 is arranged. Namely, the jaw 11 moves in a direction (closing direction) approaching an end portion 121 (FIG. 1 and FIG. 2) of the vibration transmission portion 12 at the distal end side Ar1.

Furthermore, the jaw 11 rotates in the clockwise direction about the second rotation axis Rx2 in FIG. 2 in accordance with the opening operation that is performed on the movable handle 7 by the operating person, such as the operator. Namely, the jaw 11 moves in a direction (opening direction) moving away from the end portion 121 of the vibration transmission portion 12 at the distal end side Ar1.

As described above, the jaw 11 opens and closes relative to the end portion 121 of the vibration transmission portion 12 at the distal end side Ar1 in accordance with operation that is performed on the movable handle 7 by the operating person, such as the operator, and grips a target region with the end portion 121. Therefore, the jaw 11 and the end portion 121 correspond to a pair of grippers.

Furthermore, the inner pipe 14 and the slider receiver 16 are connected to the jaw 11, and move forward and backward along the central axis Ax, to thereby open and close the jaw 11. Therefore, the inner pipe 14 and the slider receiver 16 correspond to a transmission portion.

Moreover, the coil spring 19 is compressively deformed in accordance with an operating force that is applied to the movable handle 7 in accordance with the closing operation that is performed on the movable handle 7 by the operating person, such as the operator, and transmits the operating force to the slider receiver 16. Therefore, the coil spring 19 corresponds to an elastic body. Furthermore, the coil spring 19 is used to maintain a constant gripping force for gripping the target region between the jaw 11 and the end portion 121 of the vibration transmission portion 12 at the distal end side Ar1.

Here, it is assumed that the operating person, such as the operator, performs the closing operation on the movable handle 7 (operation for moving the movable handle 7 at a maximum until the movable handle 7 approaches the fixed handle 62). In this case, the gripping force between the jaw 11 and the end portion 121 of the vibration transmission portion 12 at the distal end side Ar1 varies depending on an amount of compressive deformation of the coil spring 19.

Further, the adjustment mechanism 18 adjusts the gripping force between the jaw 11 and the end portion 121 by adjusting the amount of compressive deformation of the coil spring 19.

Meanwhile, a detailed configuration of the adjustment mechanism 18 will be described later.

At least a part of the jaw 11 is configured with a conductive material.

The vibration transmission portion 12 is configured with a conductive material, and has an elongated shape that linearly extends along the central axis Ax. Further, as illustrated in FIG. 2, the vibration transmission portion 12 is inserted in the sheath 10 while the end portion 121 at the distal end side Ar1 protrudes to the outside. In this case, an end portion of the vibration transmission portion 12 at the proximal end side Ar2 is mechanically connected to the ultrasonic transducer 5, although detailed illustration is omitted. Namely, the vibration transmission portion 12 transmits ultrasonic vibration that is generated by the ultrasonic transducer 5 from the end portion at the proximal end side Ar2 to the end portion 121 at the distal end side Ar1. In the first embodiment, the ultrasonic vibration is longitudinal vibration that is vibration along the central axis Ax.

Meanwhile, an outer peripheral surface of the vibration transmission portion 12 is covered by an inner tube TI (FIG. 2) with electrical insulation property in order to ensure electrical insulation among the outer pipe 13, the inner pipe 14, and the vibration transmission portion 12.

As illustrated in FIG. 1, the ultrasonic transducer 5 includes a transducer (TD) case 51 and an ultrasound transducer 52.

The TD case 51 supports the ultrasound transducer 52 and is connected to the holding case main body 61 in a detachably attachable manner.

The ultrasound transducer 52 generates ultrasonic vibration under the control of the control device 3. In the first embodiment, the ultrasound transducer 52 is configured with a bolt-clamped Langevin-type transducer (BLT).

Configuration of Control Device

The control device 3 comprehensively controls operation of the treatment tool 2 via an electrical cable C (FIG. 1).

Specifically, the control device 3 detects the treatment operation that is performed on the switch 8 by the operating person, such as the operator, through the electrical cable C. Then, if the control device 3 detects the treatment operation, the control device 3 applies ultrasonic energy and high-frequency energy to a target region that is gripped between the jaw 11 and the end portion 121 of the vibration transmission portion 12 at the distal end side Ar1 through the electrical cable C. Namely, the control device 3 performs treatment on the target region.

For example, when applying the ultrasonic energy to the target region, the control device 3 supplies driving power to the ultrasound transducer 52 via the electrical cable C. Accordingly, the ultrasound transducer 52 generates longitudinal vibration (ultrasonic vibration) that is vibration in a direction along the central axis Ax. Further, the end portion 121 of the vibration transmission portion 12 at the distal end side Ar1 vibrates with predetermined amplitude due to the longitudinal vibration. Furthermore, the ultrasonic vibration is applied from the end portion 121 to the target region that is gripped between the jaw 11 and the end portion 121. In other words, the end portion 121 applies the ultrasonic energy to the target region.

Moreover, for example, when applying the high-frequency energy to the target region, the control device 3 supplies high-frequency power to a space between the jaw 11 and the vibration transmission portion 12 through the electrical cable C. Accordingly, a high-frequency current flows into the target region that is gripped between the jaw 11 and the end portion 121 of the vibration transmission portion 12 at the distal end side Ar1. In other words, the high-frequency energy is applied to the target region.

Configuration of Adjustment Mechanism

Figure 6:
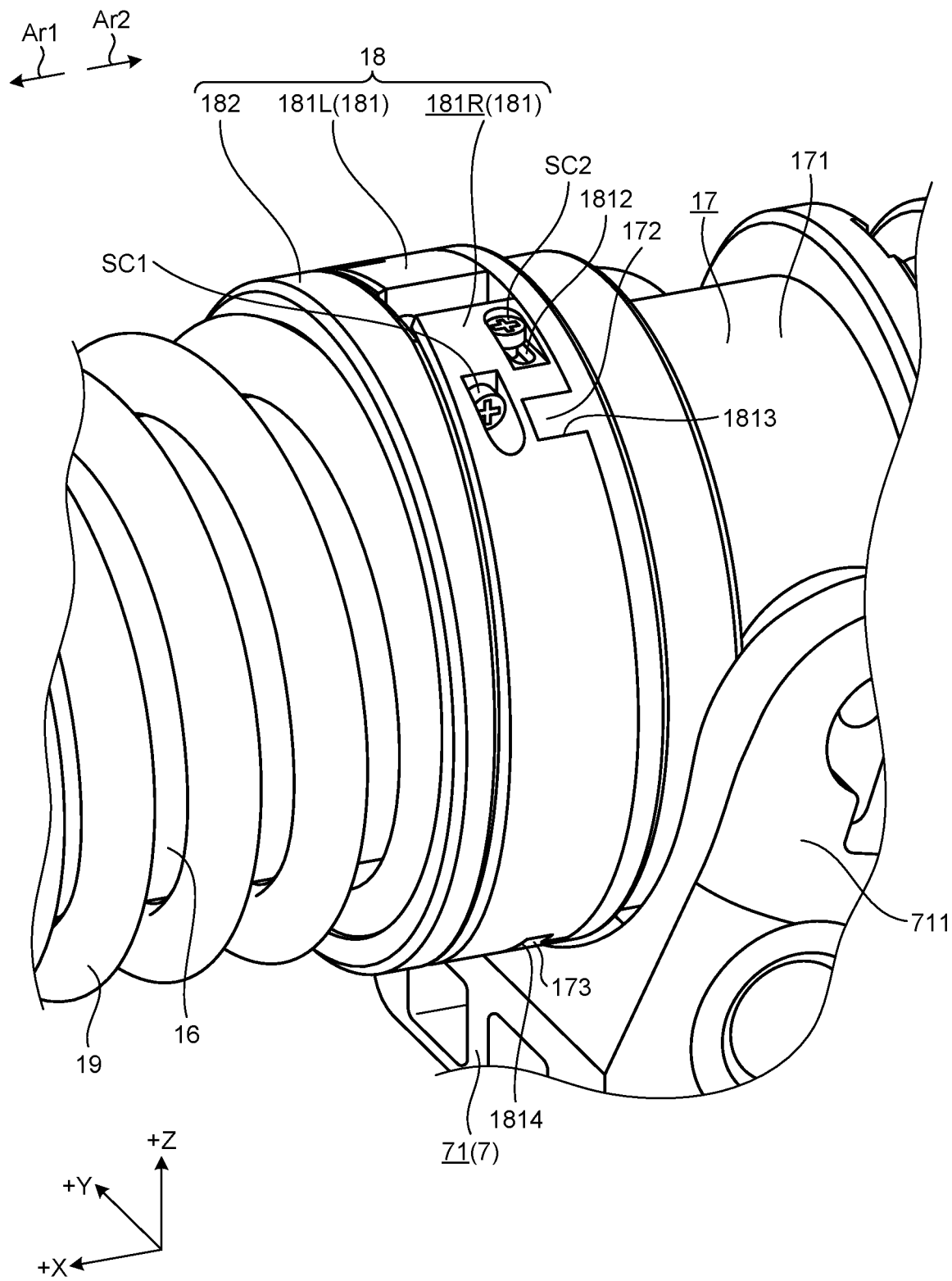
FIG. 6 is a diagram for explaining a configuration of an adjustment mechanism.
Figure 7:
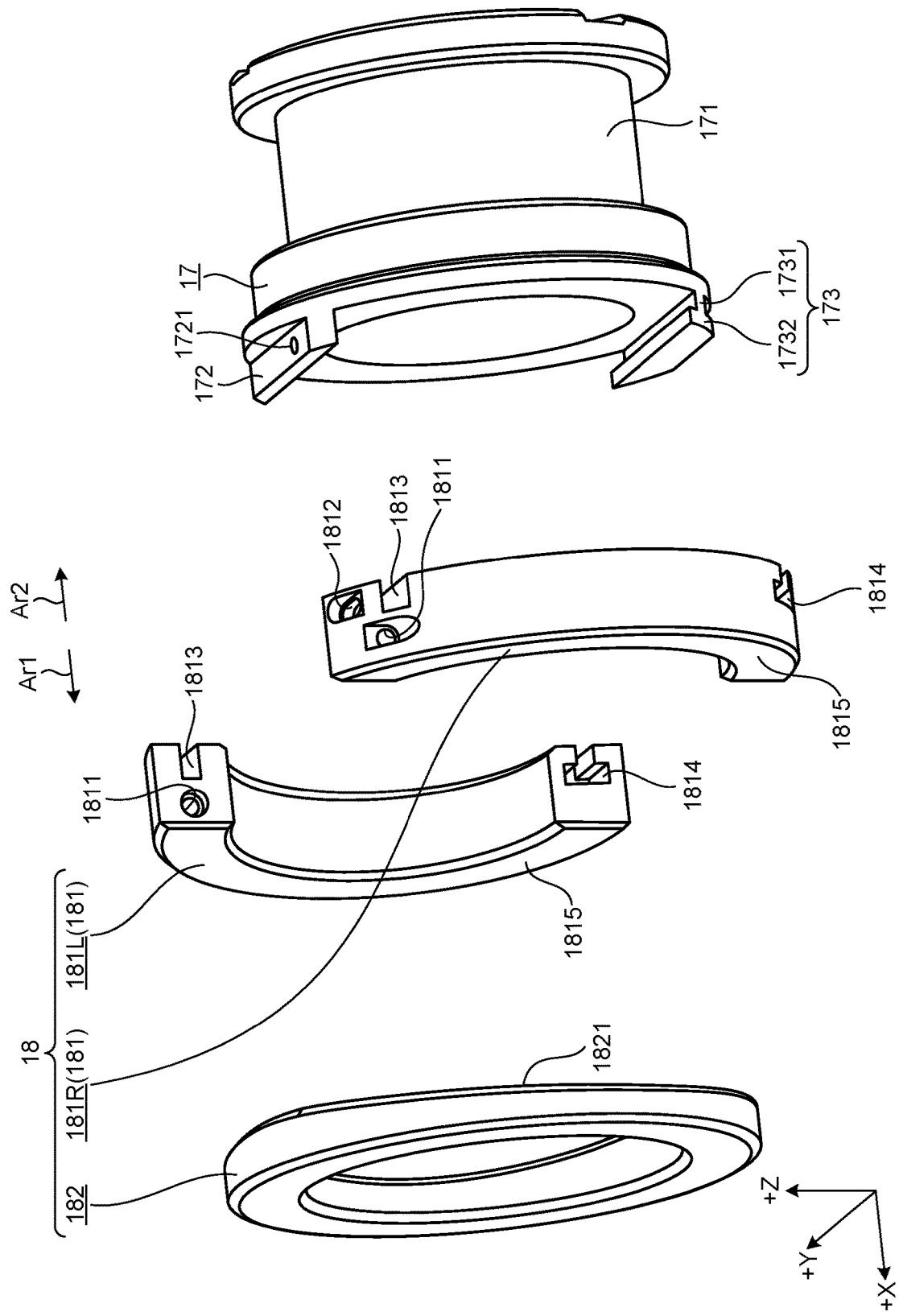
FIG. 7 is a diagram for explaining the configuration of the adjustment mechanism.
Figure 8:
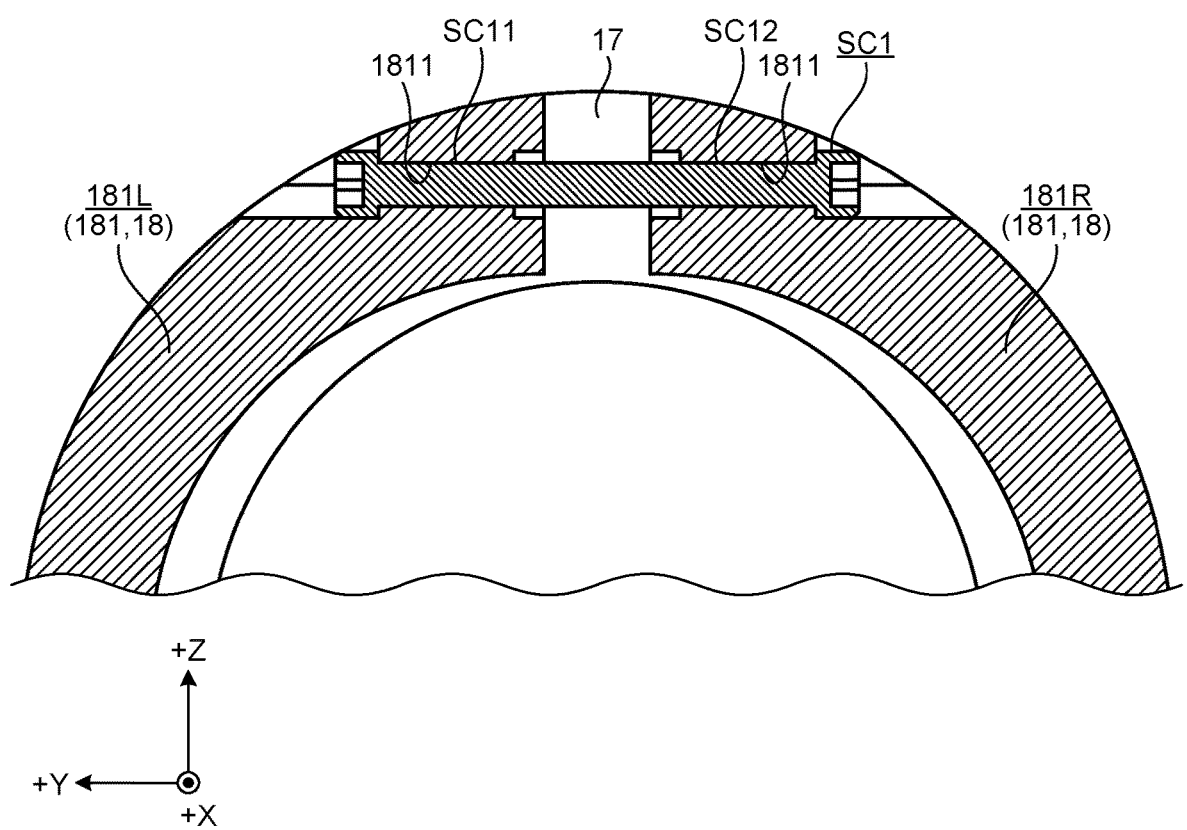
FIG. 8 is a diagram for explaining the configuration of the adjustment mechanism.
Figure 9:
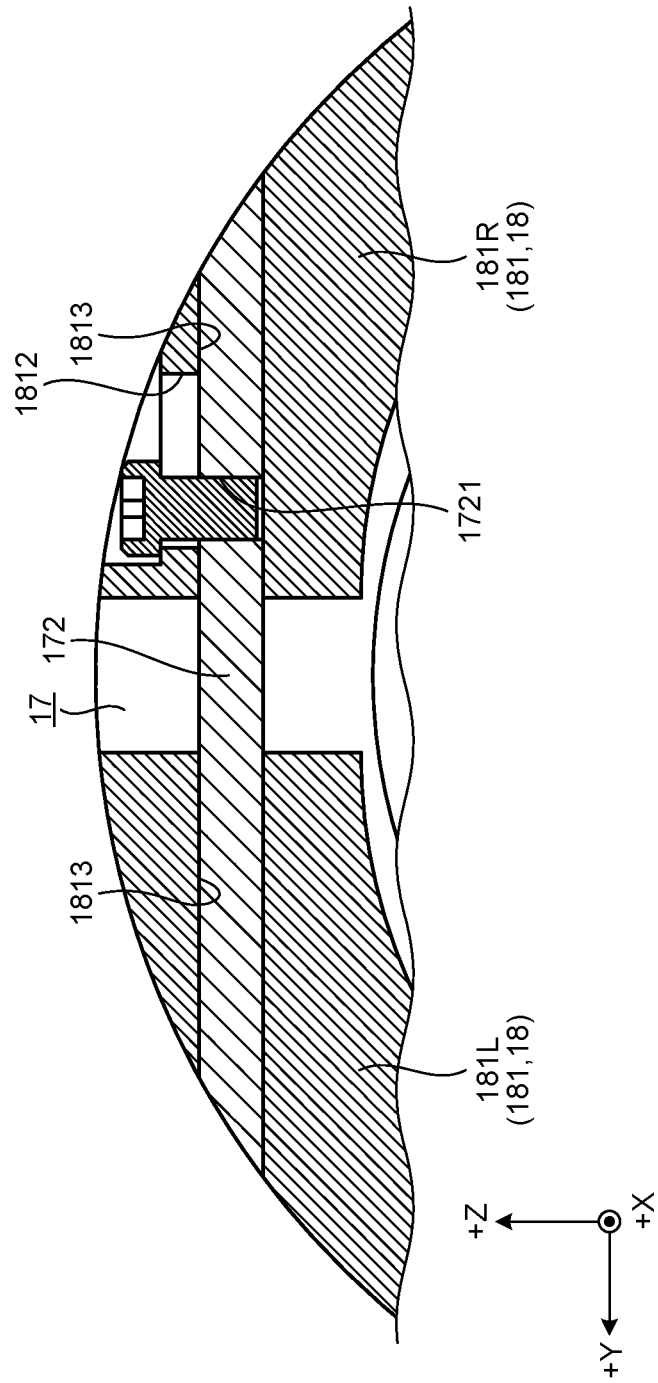
FIG. 9 is a diagram for explaining the configuration of the adjustment mechanism.

FIG. 6 to FIG. 9 are diagrams for explaining the configuration of the adjustment mechanism 18. Specifically, FIG. 6 is a perspective view illustrating a state in which the adjustment mechanism 18 is assembled to the slider 17. FIG. 7 is an exploded perspective view of the adjustment mechanism 18 and the slider 17. FIG. 8 is a cross-sectional view of the adjustment mechanism 18 taken along an YZ plane that passes through the first screw SC1. FIG. 9 is a cross-sectional view of the adjustment mechanism 18 taken along the YZ plane that passes through the second screw SC2.

In the first embodiment, the adjustment mechanism 18 is arranged between the slider 17 and the coil spring 19. Further, the adjustment mechanism 18 is assembled to an end portion of the slider 17 at the distal end side Ar1.

First, a structure of the end portion of the slider 17 at the distal end side Ar1 to which the adjustment mechanism 18 is assembled will be described before explanation of the configuration of the adjustment mechanism 18.

As illustrated in FIG. 7, a first rail 172 and a second rail 173 are arranged on an end face of the slider 17 at the distal end side Ar1.

The first rail 172 is arranged at the positive Z-axis side on the end face of the slider 17 at the distal end side Ar1. The first rail 172 protrudes from the end face of the distal end side Ar1 toward the distal end side Ar1 and extends along the Y axis. Further, a fixing hole 1721, which extends toward the negative Z-axis side and with which the second screw SC2 (to be described later) is screwed, is arranged on a surface of the first rail 172 at the positive Z-axis side.

The second rail 173 is arranged at the negative Z-axis side on the end face of the slider 17 at the distal end side Ar1. As illustrated in FIG. 7, the second rail 173 includes a base portion 1731 and a regulating piece 1732.

The base portion 1731 protrudes from the end face of the slider 17 at the distal end side Ar1 toward the distal end side Ar1 and extends along the Y axis. Namely, the base portion 1731 is parallel to the first rail 172.

The regulating piece 1732 is a portion that protrudes to the positive Y-axis side and the negative Y-axis side from a protruding end of the base portion 1731. Namely, the second rail 173 has a T-shaped cross section along an XZ plane.

As illustrated in FIG. 6 to FIG. 9, the adjustment mechanism 18 includes a pair of tables 181, a contact portion 182 (FIG. 6 and FIG. 7), the first screw SC1 (FIG. 6 and FIG. 8), and the second screw SC2 (FIG. 6 and FIG. 9).

The tables 181 as the pair are formed by separating an annular-shaped member into two bodies with respect to the XZ plane. In the following, the table 181 on the right side (negative Y-axis side) in the pair of the tables 181 when viewed from the distal end side Ar1 will be described as a table 181R, and the table 181 on the left side (positive Y-axis side) will be described as a table 181L.

As illustrated in FIG. 6 to FIG. 9, a screw hole 1811 (FIG. 7 and FIG. 8), a long hole 1812 (FIG. 6, FIG. 7, and FIG. 9), a first slit 1813 (FIG. 6, FIG. 7, and FIG. 9), and a second slit 1814 (FIG. 6 and FIG. 7) are arranged on the table 181R.

As illustrated in FIG. 7 or FIG. 8, the screw hole 1811 is a hole that penetrates through the table 181R along the Y axis and with which the first screw SC1 is screwed.

As illustrated in FIG. 6, FIG. 7, or FIG. 9, the first slit 1813 is arranged in a portion facing the first rail 172 on an end face of the table 181R at the proximal end side Ar2. The first slit 1813 is recessed from the end face of the table 181R at the proximal end side Ar2 toward the distal end side Ar1, and penetrates through the table 181R along the Y axis. Further, a cross-sectional shape of the first slit 1813 cut along the XZ plane conforms to the cross-sectional shape of the first rail 172 cut along the XZ plane. Furthermore, the first rail 172 is inserted in the first slit 1813.

As illustrated in FIG. 6, FIG. 7, or FIG. 9, the long hole 1812 is a long hole that penetrates to the first slit 1813 from the positive Z-axis side of the table 181R and that extends along the Y axis. Further, the second screw SC2 is inserted in the long hole 1812.

As illustrated in FIG. 6 or FIG. 7, the second slit 1814 is arranged in a portion facing the second rail 173 on the end face of the table 181R at the proximal end side Ar2. The second slit 1814 is recessed from the end face of the table 181R at the proximal end side Ar2 toward the distal end side Ar1, and penetrates through the table 181R along the Y axis. Further, a cross-sectional shape of the second slit 1814 cut along the XZ plane conforms to the cross-sectional shape of the second rail 173 cut along the XZ plane. Furthermore, the second rail 173 is inserted in the second slit 1814.

Figure 10:
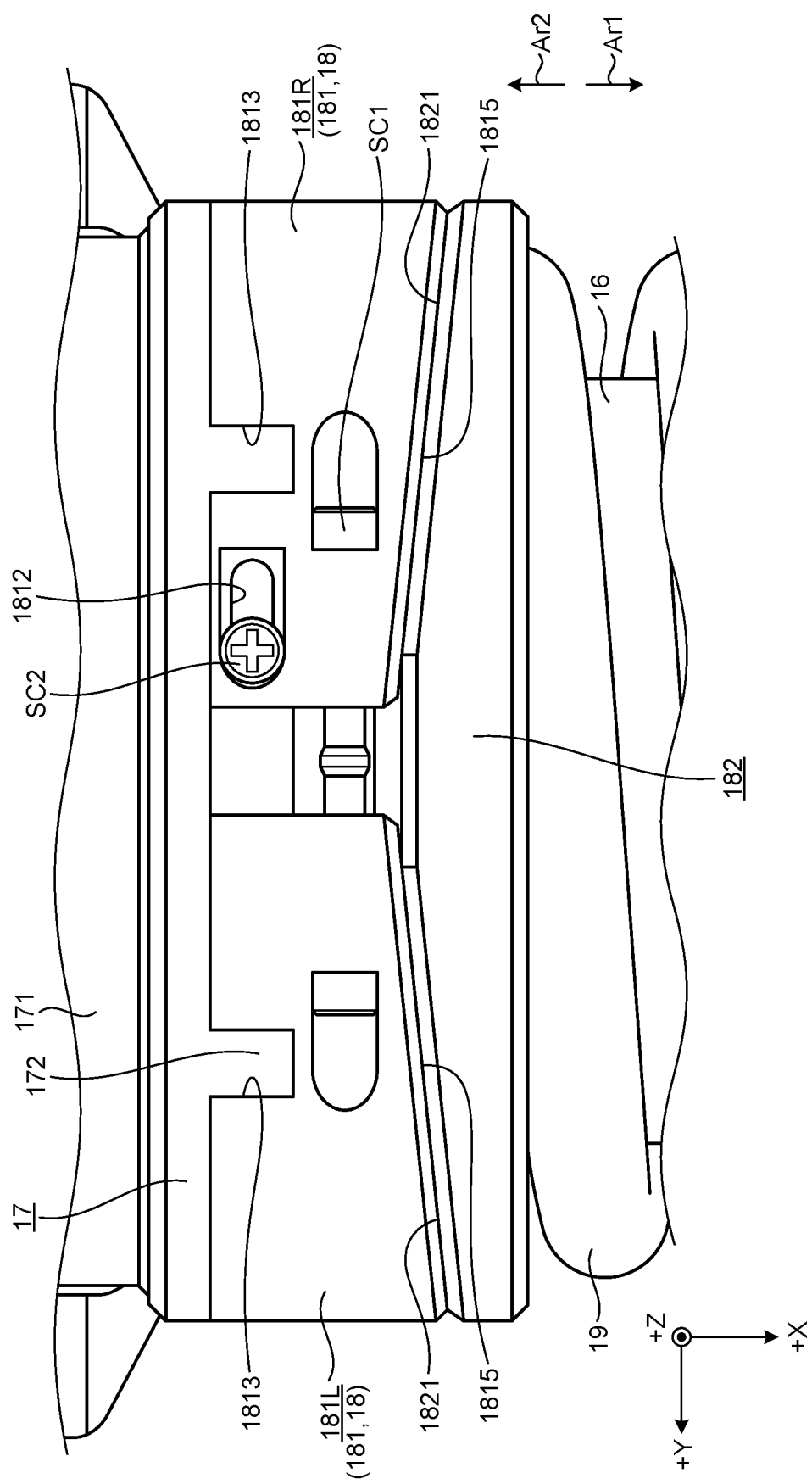
FIG. 10 is a diagram for explaining operation of the adjustment mechanism.
Figure 11:
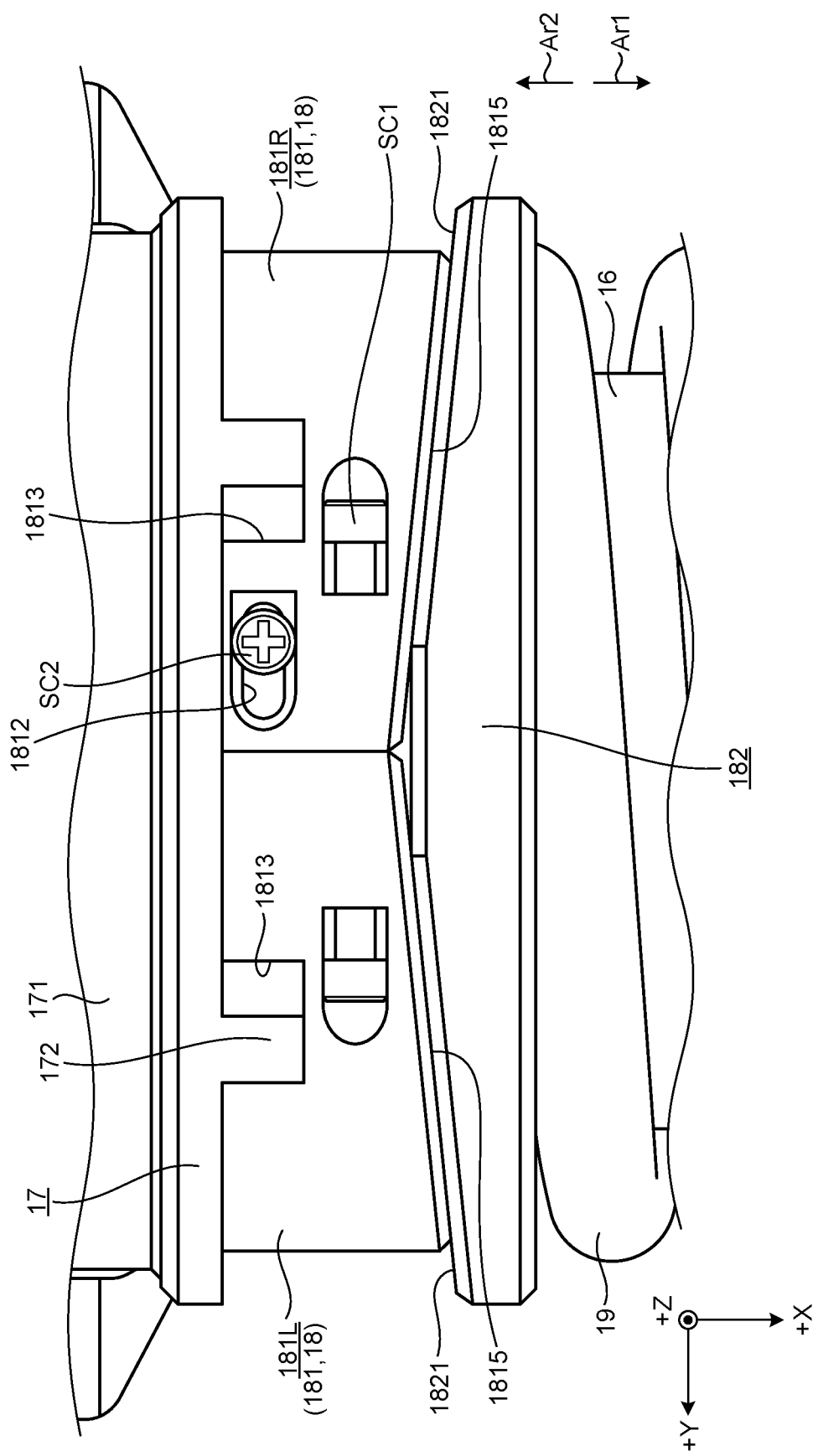
FIG. 11 is a diagram for explaining the operation of the adjustment mechanism.

Moreover, an end face of the table 181R at the distal end side Ar1 is configured with a first inclined surface 1815 that is inclined toward the distal end side Ar1 along the negative Y-axis side (see FIG. 10 and FIG. 11).

The table 181L and the table 181R have symmetric shapes with respect to the XZ plane. Meanwhile, the long hole 1812 is not arranged in the table 181L.

The tables 181 as the pair as described above are assembled to the slider 17 in a state in which the first rail 172 and the second rail 173 are inserted in the first slits 1813 and the second slits 1814 and the slider receiver 16 is inserted between the tables 181 as the pair.

As illustrated in FIG. 6 or FIG. 7, the contact portion 182 has an annular shape, and is arranged between the pair of tables 181 and the coil spring 19 in a state in which the slider receiver 16 is inserted in the contact portion 182. Further, the contact portion 182 comes into contact with the coil spring 19. Second inclined surfaces 1821 as a pair (see FIG. 10 and FIG. 11) that come into contact with the first inclined surfaces 1815 of the tables 181 as the pair are arranged on an end face of the contact portion 182 at the proximal end side Ar2.

The first screw SC1 corresponds to a screw. As illustrated in FIG. 6 or FIG. 8, the first screw SC1 is screwed with the screw holes 1811 in the tables 181 as the pair. More specifically, as illustrated in FIG. 8, the first screw SC1 is a screw in which a normal-thread screw SC11 that is screwed with the screw hole 1811 in the table 181L and a reverse-thread screw SC12 that is screwed with the screw hole 1811 in the table 181R are integrated.

As illustrated in FIG. 6 or FIG. 9, the second screw SC2 is a member that is screwed with the fixing hole 1721 through the long hole 1812 and fixes the pair of tables 181 to the slider 17. Namely, the second screw SC2 corresponds to a fixing portion.

Operation of Adjustment Mechanism

FIG. 10 and FIG. 11 are diagrams for explaining operation of the adjustment mechanism 18.

The operation of the adjustment mechanism 18 as described above will be described below.

First, the operator inserts a tool, such as a driver, into the first through hole 611 that is arranged in the holding case 6, and rotates the first screw SC1 by the tool.

For example, if the first screw SC1 is rotated in the clockwise direction when viewed from the negative Y-axis side, the tables 181 as the pair are guided along the first rail 172 and the second rail 173 and move in directions approaching each other (from the state illustrated in FIG. 10 to the state illustrated in FIG. 11). Accordingly, the contact portion 182 moves to the distal end side Ar1. Namely, when the operating person, such as the operator, performs the closing operation on the movable handle 7 (operation of moving the movable handle 7 at a maximum until the movable handle 7 approaches the fixed handle 62), a separation distance between the contact portion 182 and the opposing portion 161 is reduced. That is, in this case, the amount of compressive deformation of the coil spring 19 is increased. In other words, the gripping force between the jaw 11 and the end portion 121 of the vibration transmission portion 12 at the distal end side Ar1 is increased.

In contrast, if the first screw SC1 is rotated in the counterclockwise direction when viewed from the negative Y-axis side, the tables 181 as the pair are guided by the first rail 172 and the second rail 173 and move in directions moving away from each other (from the state illustrated in FIG. 11 to the state illustrated in FIG. 10). Accordingly, the contact portion 182 moves to the proximal end side Ar2. Namely, when the operating person, such as the operator, performs the closing operation on the movable handle 7 (operation of moving the movable handle 7 at a maximum until the movable handle 7 approaches the fixed handle 62), a separation distance between the contact portion 182 and the opposing portion 161 is increased. That is, in this case, the amount of compressive deformation of the coil spring 19 is reduced. In other words, the gripping force between the jaw 11 and the end portion 121 of the vibration transmission portion 12 at the distal end side Ar1 is reduced.

Furthermore, the operator adjusts the gripping force between the jaw 11 and the end portion 121 of the vibration transmission portion 12 at the distal end side Ar1 as described above, and thereafter uses the tool, such as the driver. Namely, the operator inserts the tool into the second through hole 612 that is arranged in the holding case 6, and fastens the second screw SC2 to the fixing hole 1721 by using the tool. Consequently, the separation distance between the tables 181 as the pair is fixed. In other words, the gripping force between the jaw 11 and the end portion 121 of the vibration transmission portion 12 at the distal end side Ar1 is maintained at the adjusted gripping force as described above.

Treatment Tool Assembly Method

Figure 12:
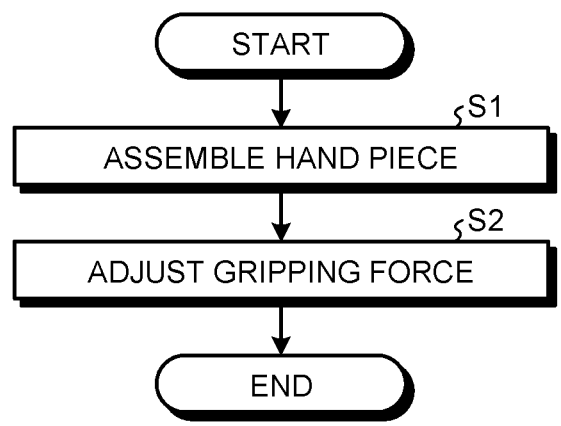
FIG. 12 is a flowchart illustrating a treatment tool assembly method.

FIG. 12 is a flowchart illustrating a method of assembling the treatment tool 2.

The method of assembling the treatment tool 2 as described above will be described below.

First, the operator assembles the hand piece 4 (Step S1).

Specifically, the operator performs a process of constructing the sheath 10 by assembling the outer pipe 13, the inner pipe 14, the holder portion 15, the slider receiver 16, the slider 17, and the adjustment mechanism 18. The process includes a "process of assembling an adjustment mechanism to the transmission portion". Subsequently, the operator performs a process of inserting the vibration transmission portion 12 into the sheath 10 from the proximal end side Ar2 of the sheath 10 (the holder portion 15). Then, the operator performs a process of assembling the jaw 11 to the outer pipe 13 and the inner pipe 14. The process corresponds to a "process of assembling at least one of grippers to the transmission portion". Further, the operator performs a process of constructing the hand piece 4 by assembling the movable handle 7, the holding case 6, the switch 8, and the rotation knob 9 to the slider 17. The process includes a "process of assembling an operating portion to the transmission portion".

Then, the operator performs a process explained in the "operation of the adjustment mechanism" as described above to adjust the gripping force between the jaw 11 and the end portion 121 of the vibration transmission portion 12 at the distal end side Ar1 to a specific gripping force (Step S2).

According to the first embodiment as described above, it is possible to achieve effects as described below.

The treatment tool 2 according to the first embodiment includes the adjustment mechanism 18, so that it is possible to adjust the gripping force between the jaw 11 and the end portion 121 of the vibration transmission portion 12 at the distal end side Ar1. Therefore, even if the gripping force between the jaw 11 and the end portion 121 does not fall in a range of a standard value after the hand piece 4 is constructed, it is not necessary to discard the hand piece 4 or modify the gripping force such that the gripping force falls in the range of the standard value.

In particular, the adjustment mechanism 18 includes the pair of tables 181, the contact portion 182, and the first screw SC1. Therefore, the operator is able to bring the tables 181 as the pair closer to or away from each other by only rotating the first screw SC1, and is able to easily adjust the gripping force between the jaw 11 and the end portion 121 of the vibration transmission portion 12 at the distal end side Ar1.

Furthermore, the adjustment mechanism 18 includes the second screw SC2, so that it is possible to maintain the adjusted gripping force in a preferable manner.

Moreover, the adjustment mechanism 18 is accessible via the first through hole 611 and the second through hole 612 that are arranged in the holding case 6, so that it is possible to prevent the operator or the like from arbitrarily changing the gripping force.

Second Embodiment

A second embodiment will be described below.

In the following description, the same components as those of the first embodiment as described above are denoted by the same reference symbols, and detailed explanation thereof will be omitted or simplified.

Figure 13:
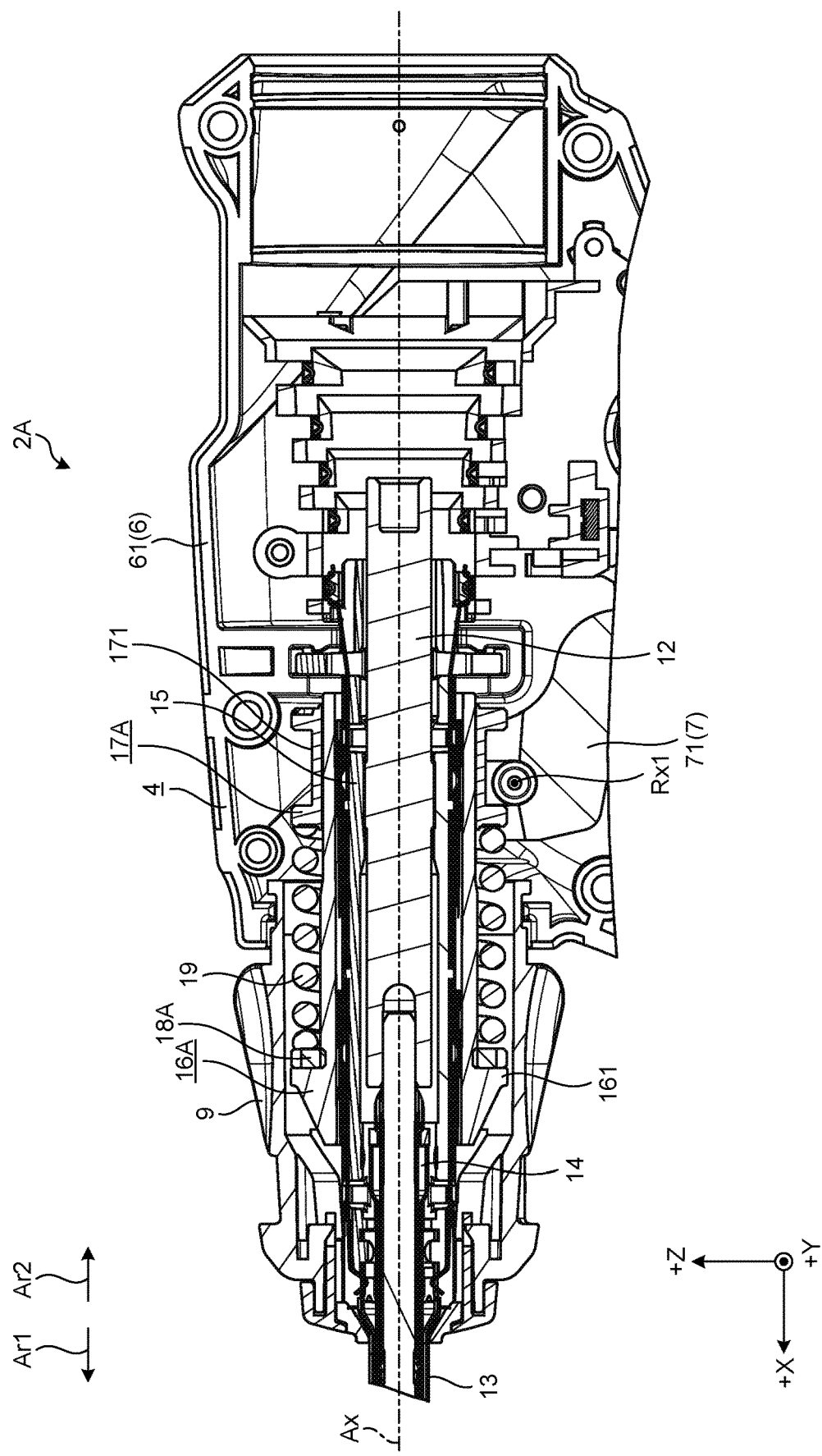
FIG. 13 is a diagram for explaining a configuration of an adjustment mechanism according to a second embodiment.

FIG. 13 is a diagram for explaining a configuration of the adjustment mechanism 18 according to the second embodiment. Specifically, FIG. 13 is a cross-sectional view corresponding to FIG. 5.

The second embodiment is different from the first embodiment as described above in that the slider receiver 16 and the slider 17 have different shapes and the adjustment mechanism 18 are arranged at a different position and has a different configuration.

In the following, for convenience of explanation, the treatment tool 2, the slider receiver 16, the slider 17, and the adjustment mechanism 18 according to the second embodiment will be described as a treatment tool 2A, a slider receiver 16A, a slider 17A, and an adjustment mechanism 18A, respectively. In the second embodiment, the slider receiver 16A and the inner pipe 14 correspond to the transmission portion.

As illustrated in FIG. 13, the adjustment mechanism 18A is a nut having an annular shape, and is arranged between the opposing portion 161 and the coil spring 19.

Namely, in the slider 17A, the first rail 172 and the second rail 173 of the slider 17 explained in the first embodiment as described above are omitted. Further, in the slider receiver 16A, a screw thread (not illustrated) with which the adjustment mechanism 18A is screwed is formed on a portion of an outer peripheral surface at the distal end side Ar1, as compared to the slider receiver 16 explained in the first embodiment as described above. Namely, the adjustment mechanism 18A is configured with a screw that comes into contact with the coil spring 19 and screws with the slider receiver 16A.

Furthermore, the position of the adjustment mechanism 18A is changed by changing a screwed state with respect to the slider receiver 16A. With this configuration, a separation distance between the adjustment mechanism 18A and the slider 17 is changed when the operating person, such as the operator, performs the closing operation on the movable handle 7 (operation of moving the movable handle 7 at a maximum until the movable handle 7 approaches the fixed handle 62). Namely, the amount of compressive deformation of the coil spring 19 in this case is changed. In other words, the gripping force between the jaw 11 and the end portion 121 of the vibration transmission portion 12 at the distal end side Ar1 in this case is changed.

Meanwhile, as a configuration for changing the screwed state of the adjustment mechanism 18A with respect to the slider receiver 16A, a configuration as described below may be adopted, for example.

A slit that penetrates through inside and outside of the rotation knob 9 and that extends in the rotation direction about the central axis Ax is formed in the rotation knob 9. Further, the operator inserts a tool, such as a driver, into the slit, and rotates the rotation knob 9 by the tool while preventing the adjustment mechanism 18A from rotating about the central axis Ax. With this configuration, the screwed state of the adjustment mechanism 18A with respect to the slider receiver 16A is changed.

According to the second embodiment as described above, it is possible to achieve effects as described below, in addition to the effects achieved by the first embodiment as described above.

The adjustment mechanism 18A according to the second embodiment is configured with only a nut having an annular shape. Therefore, it is possible to reduce the number of components and improve assembly performance of the treatment tool 2.

Other Embodiments

While the embodiments of the disclosure have been described above, the disclosure is not limited to the first and the second embodiments as described above.

In the first and the second embodiments as described above, a configuration that applies both of ultrasonic energy and high-frequency energy to a target region is adopted as the treatment tool, but embodiments are not limited to this example, and a configuration that applies at least one of ultrasonic energy, high-frequency energy, and thermal energy may be adopted. Here, "application of thermal energy to the target region" means transmission of heat that is generated by a heater or the like to the target region.

In the first and the second embodiments as described above, the gripping force is adjusted after the hand piece 4 is assembled, but embodiments are not limited to this example, and it may be possible to adjust the gripping force before the holding case 6 or the rotation knob 9 is assembled.

In the first and the second embodiments as described above, the pair of protruding portions 711 move toward the distal end side Ar1 in accordance with the closing operation that is performed on the movable handle 7 by the operating person, such as an operator, but embodiments are not limited to this example, and the pair of protruding portions 711 may be configured to move toward the proximal end side Ar2. If this configuration is adopted, the opposing portion 161, the coil spring 19, the adjustment mechanisms 18 and 18A, and the sliders 17 and 17A are arranged along the central axis As in the reverse order as compared to the first and the second embodiment as described above.

In the first embodiment as described above, the normal-thread screw SC11 and the reverse-thread screw SC12 are integrated in the first screw SC1, but embodiments are not limited to this example, and it may be possible to arrange only one of the normal-thread screw SC11 and the reverse-thread screw SC12.

In the second embodiment as described above, it may be possible to adopt the adjustment mechanism 18 instead of the adjustment mechanism 18A. In this case, the pair of tables 181 and the contact portion 182 are arranged along the central axis Ax in reverse order as compared to the first embodiment as described above.

According to the treatment tool and the treatment tool assembly method of the disclosure, it is possible to adjust a gripping force.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool comprising:
    a pair of grippers, at least one of the pair of grippers configured in an openable and closable manner;
    an operating portion;
    a transmission portion, connected to the at least one of the pair of grippers, the transmission portion configured to move in accordance with a movement of the operating portion to open and close the pair of grippers;
    an elastic body configured to transmit, to the transmission portion, an operating force applied to the operating portion, the elastic body configured to be compressively deformed in accordance with the operating force; and
    an adjustment mechanism including:
        a contact portion configured to be in contact with the elastic body; and
        a pair of tables configured to be in contact with the contact portion, the pair of tables configured to approach or separate from each other to adjust a position of the contact portion relative to the elastic body and adjust an amount of compressive deformation of the elastic body, wherein the treatment tool further comprises a slider connected to a proximal end surface of the pair of tables, and wherein a proximal surface of the contact portion is in contact with the pair of tables.

2. The treatment tool according to claim 1, wherein the adjustment mechanism further includes a first screw being screwed with at least one of the pair of tables, the first screw being configured to change a screwed state with respect to the at least one of the pair of tables to change a separation distance between the pair of tables.

3. The treatment tool according to claim 2, further comprising:
    a cover configured to form an external appearance of the treatment tool and cover the adjustment mechanism, wherein the cover includes a through hole penetrating through inside and outside of the cover, the through hole changing the screwed state of the first screw with respect to the at least one of the pair of tables.

4. The treatment tool according to claim 2, wherein the first screw is configured such that a normal-thread screw that is screwed with one of the pair of tables and a reverse-thread screw that is screwed with another one of the pair of tables are integrated.

5. The treatment tool according to claim 2, wherein the adjustment mechanism further includes a fixing portion second screw configured to fix the separation distance between the pair of tables after the separation distance is changed by the first screw.

6. The treatment tool according to claim 1, wherein the adjustment mechanism is configured with a screw configured to be in contact with the elastic body and to be screwed with the transmission portion, and wherein the screw is configured to change a position with a change of a screwed state with respect to the transmission portion, and adjust the amount of compressive deformation of the elastic body when user operation is performed on the operating portion.

7. The treatment tool according to claim 1, wherein the slider is configured to be movable relative to the transmission portion in accordance with movement of the operating portion, wherein and wherein the adjustment mechanism is arranged between the slider and the elastic body.

8. The treatment tool according to claim 7, wherein the slider includes a first rail arranged on a distal end surface of the slider, and wherein the pair of tables includes a first slit arranged on the proximal end surface of the pair of tables, wherein the first slit is arranged to face the first rail.

9. The treatment tool according to claim 8, wherein the first rail protrudes distally from the distal end surface of the slider, and wherein the first slit is recessed from the proximal end surface of the pair of tables, wherein the first rail is configured to be inserted in the first slit.

10. The treatment tool according to claim 8, wherein the slider further includes a second rail arranged on the distal end surface of the slider, and wherein the second rail extends parallel to the first rail.

11. The treatment tool according to claim 10, wherein the pair of tables further includes a second slit arranged on the proximal end surface of the pair of tables, and wherein the second rail protrudes distally from the distal end surface of the slider, the second rail is configured to be inserted in the second slit.

12. The treatment tool according to claim 1, wherein the slider configured to be movable relative to the transmission portion in accordance with movement of the operating portion, and wherein the transmission portion includes an opposing portion facing the slider across the elastic body, and wherein the adjustment mechanism is arranged between the opposing portion and the elastic body.

13. The treatment tool according to claim 1, wherein the pair of tables includes a first inclined surface, the first inclined surface outwardly inclined toward a distal end side of the transmission portion, and the contact portion includes a second inclined surface that is in contact with the first inclined surface.

14. The treatment tool according to claim 13, wherein the contact portion is configured to move to the distal end side of the transmission portion when the pair of tables approaches each other.

15. The treatment tool according to claim 1, wherein the transmission portion is configured to move distally and proximally to open and close the pair of grippers.

16. The treatment tool according to claim 1, wherein the transmission portion includes:
    an inner pipe connected to the at least one of the pair of grippers, and
    a slider receiver configured to move distally and proximally in accordance with the operating force, a distal end of the slider receiver is connected to a proximal end of the inner pipe.

17. The treatment tool according to claim 16, wherein the slider receiver includes an opposing portion facing the slider across the elastic body.

18. The treatment tool according to claim 1, wherein the elastic body includes a coil spring.

19. The treatment tool according to claim 1, wherein:
the contact portion, the pair of tables, and the slider are configured to be movable together relative to the transmission portion in accordance with movement of the operating portion; and
the pair of the tables is configured to adjust a distance between a distal surface of the contact portion and a proximal surface of the slider.

20. The treatment tool according to claim 19, wherein the operating portion comprises a movable handle, and wherein the slider is configured to contact the movable handle, the slider is configured to move distally and proximally in accordance with rotation of the movable handle.

21. A treatment tool assembly method comprising:
assembling at least one of a pair of grippers to a transmission portion;
assembling an adjustment mechanism to the transmission portion;
assembling an operating portion to the transmission portion; and
adjusting a gripping force of the at least one pair of grippers to a specific gripping force by using the adjustment mechanism, and wherein the method comprises providing a treatment tool comprising:
the at least one pair of grippers, wherein at least one of the at least one pair of grippers is configured in an openable and closable manner;
the operating portion;
the transmission portion connected to the at least one of the at least one pair of grippers, the transmission portion being configured to move in accordance with a movement of the operating portion to open and close the at least one pair of grippers;
an elastic body configured to transmit, to the transmission portion, an operating force applied to the operating portion, the elastic body configured to be compressively deformed in accordance with the operating force; and
the adjustment mechanism including:
a contact portion configured to be in contact with the elastic body;
a pair of tables configured to be in contact with the contact portion, the pair of tables configured to approach or separate from each other to adjust a position of the contact portion relative to the elastic body and adjust an amount of compressive deformation of the elastic body; and
a slider connected to a proximal end surface of the pair of tables, wherein a proximal surface of the contact portion is in contact with the pair of tables.

* * * * *